United States Patent
Ye et al.

(10) Patent No.: US 6,415,921 B2
(45) Date of Patent: *Jul. 9, 2002

(54) APPARATUS TO PREVENT RADIATION SOURCE DELIVERY DEVICE FROM BEING CONTAMINATED DURING BRACHYTHERAPY PROCEDURE

(75) Inventors: Ping Ye, San Diego; Julian Aldape, Sun City, both of CA (US)

(73) Assignee: Advanced Cardiovascular Systems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/409,838

(22) Filed: Sep. 30, 1999

(51) Int. Cl.[7] .............................................. B65D 83/10
(52) U.S. Cl. ...................... 206/364; 206/438; 206/495.5
(58) Field of Search ................................ 206/438, 484, 206/364, 365, 495.5, 440

(56) References Cited

U.S. PATENT DOCUMENTS

| | | | | |
|---|---|---|---|---|
| 2,756,154 A | * | 7/1956 | Mahaffy | 206/364 |
| 3,035,691 A | * | 5/1962 | Rasmussen et al. | 206/364 |
| 3,342,326 A | * | 9/1967 | Zackheim | 206/364 |
| 3,419,137 A | * | 12/1968 | Walck, III | 206/363 |
| 3,612,038 A | * | 10/1971 | Halligan | 206/364 |
| 3,750,875 A | * | 8/1973 | Juster | 206/364 |
| 3,862,886 A | * | 1/1975 | Liner | 206/438 |
| 3,918,579 A | * | 11/1975 | Diamant | 206/303 |
| 4,296,179 A | * | 10/1981 | Wardwell | 206/439 |
| 4,359,052 A | * | 11/1982 | Staub | 206/363 |
| 4,704,177 A | * | 11/1987 | Vaillancourt | 156/226 |
| 5,147,341 A | * | 9/1992 | Starke et al. | 604/349 |
| 5,217,772 A | * | 6/1993 | Brown et al. | 206/813 |
| 5,895,374 A | * | 4/1999 | Rodsten | 206/364 |
| 6,059,107 A | * | 5/2000 | Nosted et al. | 206/364 |

* cited by examiner

Primary Examiner—Shian Luong
(74) Attorney, Agent, or Firm—Blakely, Sokoloff, Taylor & Zafman LLP (57) ABSTRACT

The present invention includes a peel-away protective cover to help prevent contamination of a connector prior to insertion into a radiation source delivery device. The protective cover comprises a top sheet and a bottom sheet that are sealed together to create a protective pouch within which a connector may be positioned. The top sheet and bottom sheet may be peeled away in a proximal to distal direction in order to expose the connector for insertion into a radiation source delivery device. The proximal to distal peel-away directs any contaminants present on the protective cover away from the exposed connector. In one embodiment, the protective cover may be completely peeled away from the connector. In another embodiment, the protective cover may be partially peeled away so that the separated top and bottom sheets shield the connection to the radiation source delivery device.

27 Claims, 7 Drawing Sheets

APPARATUS TO PREVENT RADIATION SOURCE DELIVERY DEVICE FROM BEING CONTAMINATED DURING BRACHYTHERAPY PROCEDURE

FIELD OF THE INVENTION

The present invention relates to the field of protective devices for medical apparatus. In particular, the present invention relates to a protective device for use on the connector ends of catheters used with radiation source delivery devices used in intravascular radiation therapy.

DESCRIPTION OF RELATED ART

Currently, many intravascular procedures require insertion of catheters into the vessel of a patient to provide a selected treatment to a target area of the vessel. For example, a patient may require a balloon angioplasty procedure to dilate a vessel narrowed by atherosclerosis. This procedure is performed by inserting a balloon dilation catheter into the vessel of a patient, positioning the balloon dilation segment of the catheter within the constricted portion of the vessel, dilating the vessel, and then removing the dilation catheter from the patient. Often this procedure is followed by radiation therapy to prevent restenosis, or renarrowing, of the vessel area that was dilated by the angioplasty procedure.

Some radiation therapy procedures are also intravascular. For example, a prescribed dose of radiation may be administered using a catheter connected to a radiation source delivery device. The catheter typically has a treatment segment at the distal end that is positioned within the dilated vessel of the patient. The treatment segment receives a radiation source delivered through the lumen of the catheter. A connector located at the proximal end of the catheter attaches to the radiation source delivery device, such as an afterloader. In some instances, the connector may simply attach externally to the radiation delivery device to form the connection, for example, by attaching to a connection port. In other instances, the connector may be inserted into the radiation delivery device to form the connection, for example, by inserting into a connection port in a key-like manner.

Generally, the catheter is first positioned within the dilated portion of the vessel and then the connector is attached to the radiation source delivery device. The radiation source delivery device advances a radiation source through the catheter to the treatment segment and delivers the prescribed radiation dose to the vessel. After delivery of the prescribed dose, the radiation source delivery device withdraws the radiation source from the catheter, the catheter is disconnected from the radiation source delivery device, and then the catheter is withdrawn from the patient.

Intravascular procedures which utilize catheters, such as those described above, are often carried out under low light conditions to aid in positioning the catheters within the vessel. Typically, catheter positioning is performed using radioimagery methods, such as fluoroscopy, in which the location of radio-opaque markers on the catheter are used to position the catheter within the vessel. Further, during insertion of the catheter into the patient, there is frequently blood and other fluids, such as saline, that are present in the procedure area and on the gloves of the medical team. Under these conditions, it is possible for the catheter connector to become contaminated by blood or fluids prior to attachment to the radiation source delivery device.

As the radiation source delivery device is nonsterile and is for multiple use, any contamination of the device requires that the device be removed from operation and cleaned prior to continued use. Cleaning and service of the radiation source delivery device can be expensive and time consuming and removes a needed system from use by other patients. If the catheter connector becomes contaminated and is then attached to the radiation source delivery device, there is the possibility of the contaminants entering the radiation source delivery device and causing a malfunction during the procedure. Some medical teams currently wrap a towel around the catheter connector prior to attachment to the radiation source delivery device to protect the connector and the radiation source delivery device from contamination. However, under the low light conditions and in limited operating space, it becomes time consuming and cumbersome to ensure the catheter connector remains covered during catheter positioning within the patient.

Thus, a need exists to help prevent contamination of the radiation source delivery device by the connector that is easy to use and does not encumber the intravascular procedure.

SUMMARY OF THE INVENTION

The present invention includes a peel-away protective cover to help prevent contamination of a connector prior to attachment to a radiation source delivery device. The protective cover comprises a top sheet and a bottom sheet that are sealed together to create a protective pouch within which a connector may be positioned. The top sheet and bottom sheet may be peeled away in a proximal to distal direction in order to expose the connector for attachment to a radiation source delivery device. The proximal to distal peel-away directs any contaminants present on the protective cover away from the exposed connector. In one embodiment, the protective cover may be completely peeled away from the connector. In another embodiment, the protective cover may be partially peeled away so that the separated top and bottom sheets of the protective cover shield the connection to the radiation source delivery device.

BRIEF DESCRIPTION OF THE DRAWINGS

The present invention may best be understood by referring to the following description and accompanying drawings which are used to illustrate embodiments of the invention. In the drawings.

DETAILED DESCRIPTION OF THE PREFERRED EMBODIMENT

The present invention provides a peel-away protective cover that helps to prevent contamination of a catheter connector and radiation source delivery device during an intravascular procedure. The present invention may also be used to shield the connection to the radiation source delivery device from contamination during a radiation therapy procedure. In the following embodiments and examples, the present invention is described in relation to delivery of intravascular radiation therapy (IRT) utilizing a catheter and a radiation source delivery device. It is to be understood that the present invention may be used to protect a catheter connector from contamination prior to connection to devices other than radiation source delivery devices. Further, the present invention may also be used with intravascular procedures other than IRT where it is advantageous to prevent contamination of catheter connectors, or other connectors, used in those procedures, for example, angioplasty, atherectomy, stenting, or instrumental diagnostic procedures.

Figure 1:
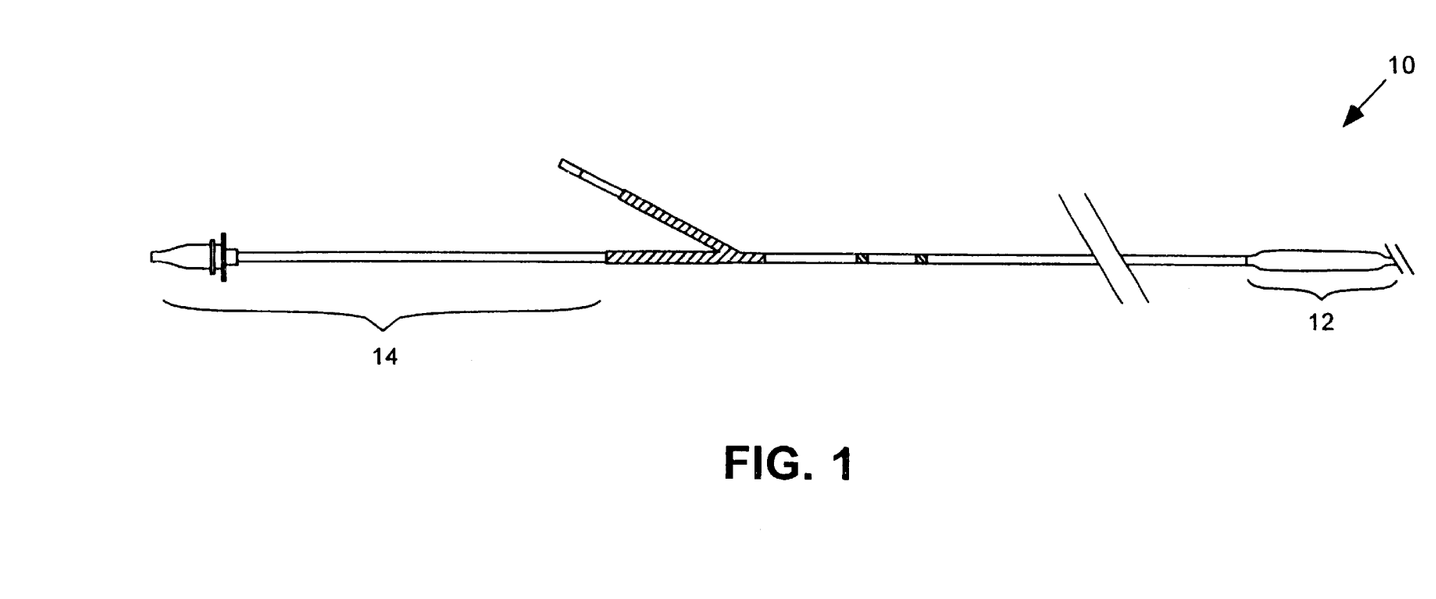
FIG. 1 illustrates a general example of an IRT catheter prior to connection to a radiation source delivery device for use in delivery of intravascular radiation therapy.

FIG. 1 illustrates a general example of a catheter prior to connection to a radiation source delivery device for use in delivery of intravascular radiation therapy. Typically, the catheter 10 has a distal treatment segment 12 that is positioned within the vessel of the patient and a connector 14 located at the proximal end that attaches to a radiation source delivery device, such as an afterloader. Generally, the distal treatment segment 12 of the catheter is designed to maintain a position within a patient's vessel and to accept a radiation source from the radiation source delivery device to allow delivery of a prescribed dose of radiation.

The connector 14 may be a defined connector structure as shown, or may be another defined structure, for example, a key-like structure. The connector 14 may also be a less defined structure, such as the terminal end of the catheter 10, i.e., the open end of a tube. It is to be understood that the design of the connector 14 is not meant to be a limitation upon the present invention.

The connector 14 may connect to the radiation source delivery device by insertion into a connection port on the radiation source delivery device or may simply attach to the exterior of the connection port. In either case, should the connector 14 become contaminated prior to connection, the contaminants could enter the radiation source delivery device upon connection. This could lead to a malfunction of the radiation source delivery device requiring the procedure to be stopped and the device repaired and/or cleaned. Or, if the contamination is detected prior to connection, the catheter 10 may need to be withdrawn from the patient and a new catheter inserted to prevent contamination of the radiation source delivery device. In either instance, the patient is subjected to additional risks, stress and discomfort in an already stressful procedure. Further, as radiation source delivery devices are typically used to deliver radiation to several different patients, repair and cleaning of the radiation source delivery device temporarily removes a needed treatment asset from service to other patients.

Figure 2:
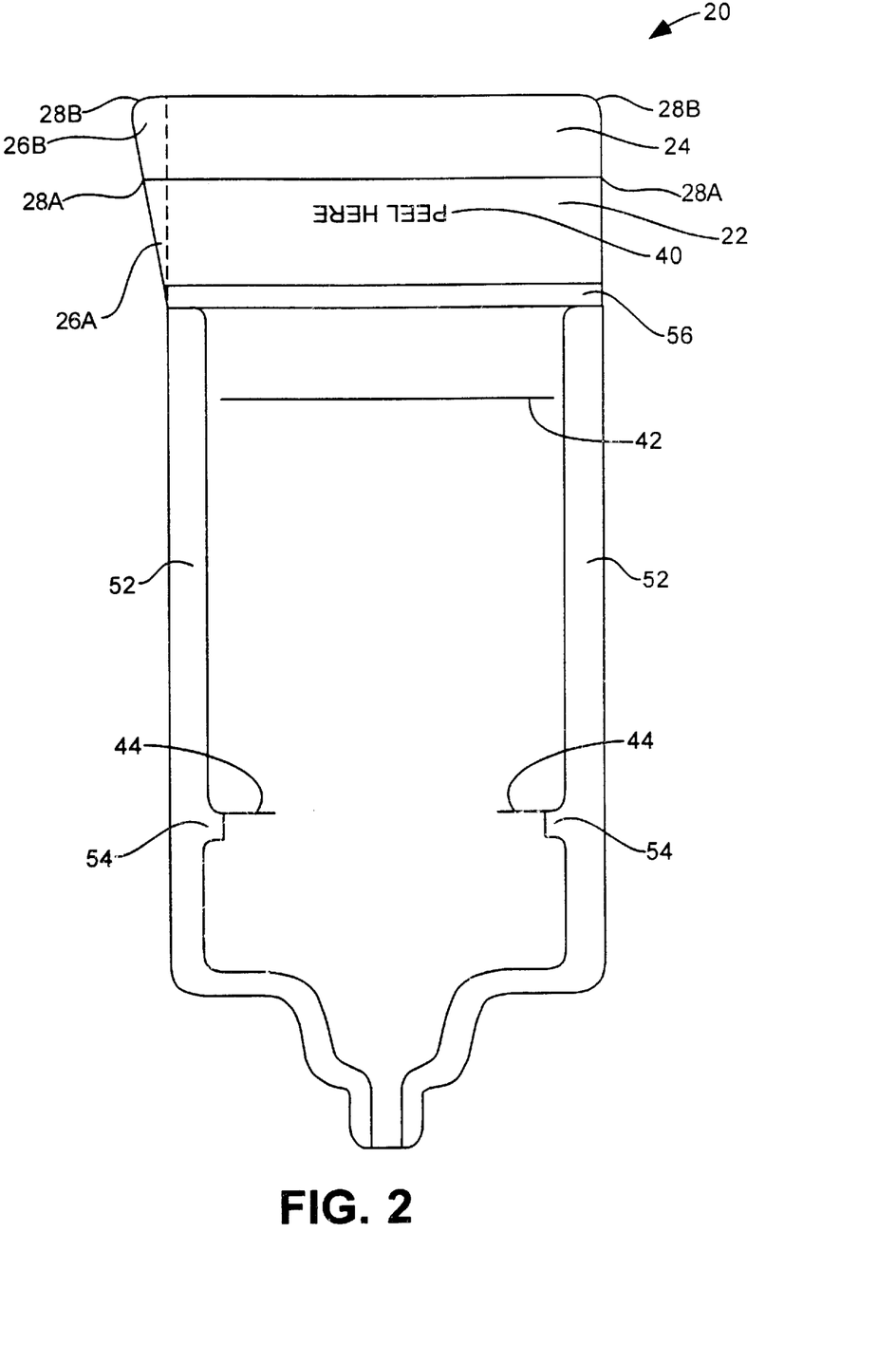
FIG. 2 illustrates a top view of a protective cover according to one embodiment of the present invention.

FIG. 2 illustrates a top view of a protective cover according to one embodiment of the present invention. In one embodiment, the protective cover 20 includes a top sheet 22 sealed to a bottom sheet 24 so as to create a protective pouch. FIG. 2 illustrates the protective cover 20 of the present invention by itself without showing a connector therein so that the following discussion of the protective cover 20 is clearer.

Although the embodiment of the present invention illustrated in FIG. 2 shows the top sheet 22 and bottom sheet 24 to be similarly sized, it is to be understood that other embodiments in which the top sheet 22 and bottom sheet 24 are differently sized may also be formed. In one embodiment, the bottom sheet 22 may be much wider than the top sheet 22 such that the protective pouch and seals may be centrally located on the bottom sheet 24.

In one embodiment, the top sheet 22 may be fabricated from a clear, flexible material, such as a waterproof 2-ply material of 200 LDPE (low density polyethylene) and 48 gauge PET (polyethylene terephthalate). Use of a clear material allows a pouched connector to be easily viewed. Other materials, clear or opaque, may be used, but it is preferable that the material chosen be water-resistant or waterproof to prevent contaminants from contacting a pouched connector. In one embodiment, the exterior face of the top sheet 22 may be 48 gauge PET and the interior face (the side adjacent the bottom sheet 24) may be 200 LDPE. The use of the 200 LDPE provides friction to facilitate gripping the top sheet 22 when beginning the peel away of the protective cover 20 to expose the pouched connector. This is helpful during intravascular procedures where fluids, such as blood and saline, may be present on the surgical gloves of a user. It is to be understood that the top sheet 22 may be fabricated using other materials, such as other 2-ply materials, single ply materials, or multiple layer materials, and that the specific materials described above are meant to be merely exemplary and not limiting of the present invention. However, no matter what material is used, it is preferred that the interior face be fabricated from a material, or coated with a film, that provides some friction to facilitate gripping of the top sheet 22.

In one embodiment, the top sheet 22 may be shorter in length at the proximal end than the bottom sheet 24 to provide an easily located start point for peel-away of the top sheet 22 from the bottom sheet 24. It is to be understood that in other embodiments the top sheet may be longer in length at the proximal end than bottom sheet, or that the top sheet 22 and bottom sheet 24 may be the same length.

Further, in one embodiment, the top sheet 22 may have a flange extension 26A to assist a user in locating the proximal start point for peel-away of the protective cover 20. Flange extension 26A facilitates peel-away of the protective cover 20 during low light procedures. It is to be understood that in other embodiments the top sheet 22 may be fabricated without a flange extension 26A, and that the flange extension 26A may be differently shaped.

In one embodiment, the proximal corners 28A of the top sheet 22 may be fabricated with sharp edges. The sharp edges further facilitate separation and peel-away of the top sheet 22 from the bottom sheet 24 which, in one embodiment, may be fabricated with proximal corners 28B having rounded edges. It is to be understood that in other embodiments either or both the proximal corners 28A and the proximal corners 28B may be fabricated with rounded edges, sharp edges, or a differently patterned edge.

In one embodiment, the bottom sheet 24 may be fabricated from an opaque, flexible material such as water-resistant Tyvek™ 1073B with CR-27 or ITP150 coating. In one embodiment, use of an opaque material provides a background for ease of viewing a pouched connector through the top sheet 22. Other materials, clear or opaque, may be used, but it is preferable that the material chosen be water-resistant or waterproof to prevent contaminants from contacting a pouched connector. It is to be understood that in other embodiments the bottom sheet 24 may be fabricated using other materials or multiple layer materials, and that the specific materials described above are meant to be merely exemplary and not limiting of the present invention.

In one embodiment, the bottom sheet 24 may be longer in length at the proximal end than the top sheet 22 to facilitate locating the start point for peel-away of the top sheet 22 from the bottom sheet 24 to expose a connector for connection. It is to be understood that the bottom sheet 24 may be shorter in length than the top sheet, or that the bottom sheet 24 and the top sheet 22 may be the same length.

In one embodiment, the bottom sheet 24 has a flange extension 26B that assists a user in locating the proximal start point for peel-away of the protective cover 20. Flange extension 26B facilitates peel-away of the protective cover 20 during low light procedures. It is to be understood that in other embodiments the bottom sheet 24 may be fabricated without a flange extension 26B, and that the flange extension 26B may be differently shaped.

In one embodiment, the proximal corners 28B of the bottom sheet 24 may be fabricated with round edges. The round edges further facilitate separation and peel-away of the bottom sheet 24 from proximal corners 28A of the top sheet 22 which, in one embodiment, may be fabricated with sharp edges. It is to be understood that in other embodiments either or both the proximal corners 28B and the proximal corners 28A may be fabricated with rounded edges, sharp edges, or a differently patterned edge.

The bottom sheet 24 may be printed with markings and/or instructions for ease of use. In one embodiment, the interior face of the bottom sheet 24 may be printed with an instruction 40, such as "PEEL HERE", at the proximal end to instruct a user where to begin the proximal to distal peel-away of the top sheet 22 from the bottom sheet 24. Other printing, such as international symbols, may also be used and printed in other locations on the bottom sheet 24. The bottom sheet 24 may also be printed with positioning markings for positioning a connector within the protective cover 20. In one embodiment, a proximal positioning marker 42, such as a long line, may be used to indicate the location of the proximal end of the protective cover 20 and of the pouched connector. Distal markers 44, such as short lines, may be used to demarcate a connecting segment of a connector from a handle, or grip, segment of the connector that may be held when attaching the connector to an radiation source delivery device, or other device. It is to be understood that in other embodiments markings and instructions may also be printed on the exterior face of the bottom sheet 24, on either face of the top sheet 22 or may be partially or completely omitted.

In one embodiment, the top sheet 22 and bottom sheet 24 are joined by seals 52 and 56, to form the protective cover 20. In one example, the seals 52 are formed using a Verton Package Sealer N#6000005. In one example, the seals 52 may be created using a high temperature set point of 220° F. (degrees Fahrenheit)±5° F., a low temperature set point of 175° F.±5° F., and a pressure of 70 PSI±5 PSI. It is to be understood that these temperature and pressure ranges may be particular to the specific sealer given above used with the particular materials described above. Other sealers may require different ranges. Other sealing methods and settings may be used, but the seals produced should be strong enough to maintain a connector in a pouched position, and yet be weak enough to allow the top sheet 22 and bottom sheet 24 to be peeled away to expose a connector for use.

In one embodiment, the seals 52 have intermediate stops 54 which are small, inward extensions of the seals 52. Intermediate stops 54 provide added resistance during peel-away of the top sheet 22 from the bottom sheet 24. The added resistance allows a user to decide whether to stop the peel-away at the intermediate stops 54 or to continue peel-away and removal of the protective cover 20 from a connector. If the peel-away is stopped at the intermediate stops 54, a pouched connector would be exposed for connection to the radiation source delivery device. Following connection, the partially separated top sheet 22 and bottom sheet 24 may then be used to help prevent contamination of the connection during the intravascular procedure. If the peel-away is not stopped at the intermediate stops 54, a user may apply a slight more pull to overcome the added resistance of the intermediate stops 54, thus allowing the protective cover 20 may be removed altogether. It should be understood that in other embodiments, intermediate stops 54 may be separate from the seals 52.

After formation of the seals 52, a connector may be inserted between the top sheet 22 and the bottom sheet 24, positioned between the markers 42 and 44, and then the seal 56 formed. In one example, the seal 56 may be formed using a standard bar sealer well-known to those of ordinary skill in the art. While seal 56 is shown being formed at the proximal edges of seals 52, it is to be understood that seal 56 may also be formed so that it crosses seals 52. It is to be understood that the sequencing of the formation of the seals 52 and 56 is not meant to limit the scope of the present invention and that other sequencing may be used.

Figure 3:
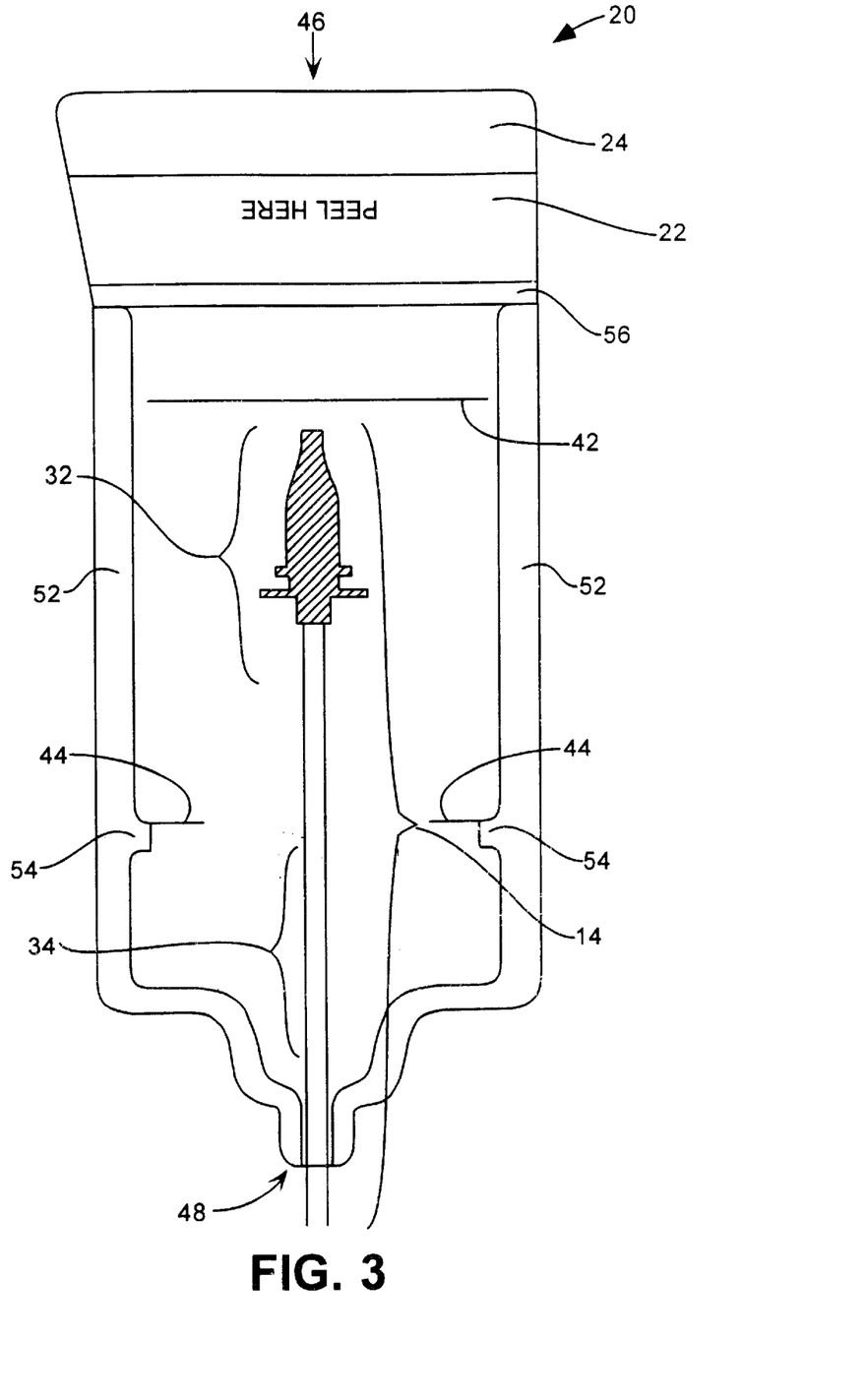
FIG. 3 illustrates a top view of a protective cover in conjunction with a connector according to one embodiment of the present invention.

FIG. 3 illustrates a top view of a protective cover in conjunction with a connector according to one embodiment of the present invention. In the present illustration, the connector 14 has a connection segment 32 for attachment to an radiation source delivery device, and a handle segment 34 that may be held while attaching the catheter to the radiation source delivery device. It is to be understood that the connector 14 is not limiting on the present invention, but rather, merely serves as an example of a connector that may be protected from contaminants by use of the present invention.

In one example, a plurality of protective covers 20 may be fabricated in a sheet format using a standard multiple, cut and seal procedure well known by those of ordinary skill in the art in which the top sheet 22 and bottom sheet 24 are cut using a die and sealed forming multiple protective covers 20 in one sheet. As earlier mentioned the Vertron Package sealer N#6000005 may be used to form the seals 52. The individual protective covers 20 are then removed from the excess materials of the sheet and are ready to be assembled with connectors. Individual connectors 14 are then inserted distal end first into the open, proximal end 46 of the protective cover 20 until the connector 14 is correctly positioned between the markers 42 and 44 and the distal end of the connector 14 exits the distal end 48 of the protective cover 20. In one embodiment, the connector 14 is correctly positioned when the handle segment 34 is distal to the intermediate stops 54 and the proximal end of the connection segment 32 is distal to the top positioning marker 42.

After positioning, the seal 56 may be formed to effectively create a protective pouch around the connector 14 so that the connector 14 is protected from contaminants prior to connection to a radiation source delivery device. In one embodiment, the seal 56 may be formed just proximal to the top positioning marker 42 so that the flange and unsealed ends of the top sheet 22 and bottom sheet 24 remain separate for ease in separately gripping each sheet during peel-away of the protective cover 20 from the connector 14. It is to be understood that other embodiments of the present invention can be fabricated in various shapes and sizes to accommodate a variety of connectors, and that the specific examples herein described are not meant to limit the scope of the present invention. Further, other methods of assembling the protective cover 20 with the connector 14 may be used, and that the method of assembly is not meant to limit the scope of the invention.

Figure 4:
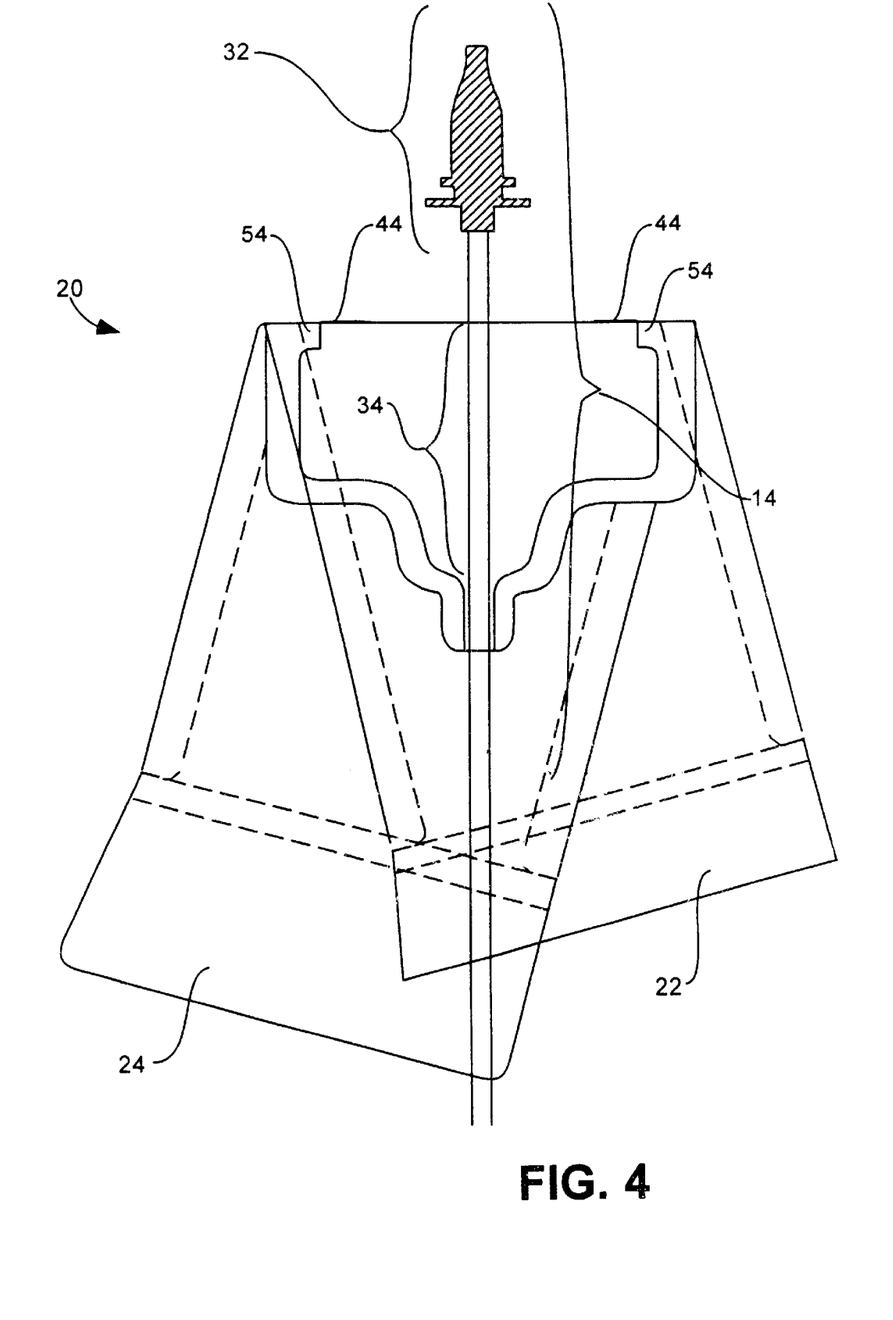
FIG. 4 illustrates one view of how a protective cover according to one embodiment of the present invention may be used in conjunction with a connector.

FIG. 4 illustrates one view of how a protective cover according to one embodiment of the present invention may be used in conjunction with a connector. FIG. 4 illustrates a protective cover 20 being partially peeled away to the intermediate stops 54. In use, a user may simultaneously and separately grip the top sheet 22 and bottom sheet 24 and peel them away from the connector 14 in a proximal to distal direction, thus breaking seal 56. Peeling the top sheet 22 away from the bottom sheet 24 in the proximal to distal direction helps to direct contaminants present on the exterior of the protective cover 20 away from the exposed connector 14.

In one embodiment, at the intermediate stops 54, the user will encounter a slight resistance due to the added width of the seals formed by the intermediate stops 54. This resistance provides a decision point for the user. If the user stops the peel-away at the intermediate stops 54, the connection segment 32 of the connector 14 is exposed and may be connected to the radiation source delivery device, and the handle segment 34 is still protected by the protective cover 20. The top sheet 22 and bottom sheet 24 separate proximal to the intermediate stops 54 in a wing-like shape to form a shielding structure. If so desired, the user may then attach the connector 14 to the radiation source delivery device so that this shielding structure helps protect the connection from contaminants during the procedure.

Alternatively, in one embodiment, the user may decide not to use the shielding feature of the present invention and may wish to simply remove the protective cover 20 from the connector 14 altogether. In this instance, the user need only apply a slight more pull to overcome the resistance of the intermediate stops 54 and continue the proximal to distal peel-away until the protective cover 20 is completely separated from the connector 14.

Figure 5:
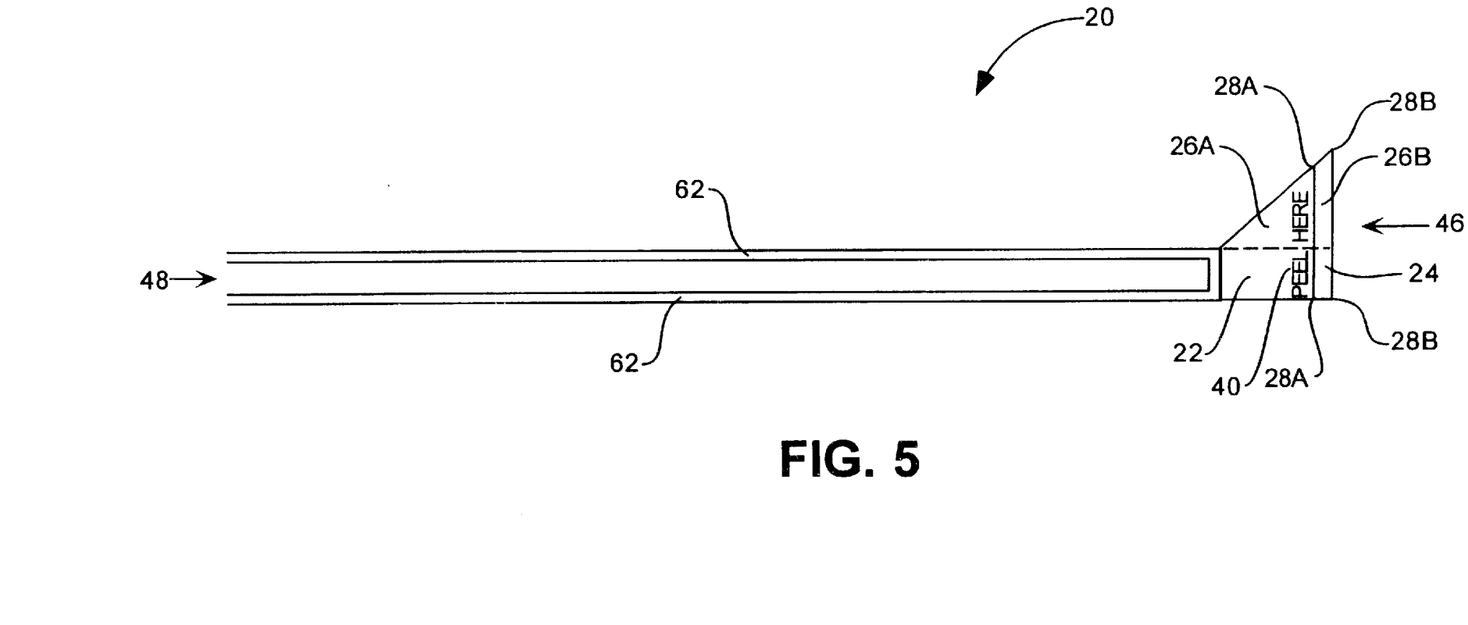
FIG. 5 illustrates a top view of a protective cover according to another embodiment of the present invention.

FIG. 5 illustrates a top view of a protective cover according to another embodiment of the present invention. In the embodiment illustrated in FIG. 5, the top sheet 22 and bottom sheet 24 may be fabricated from the same materials as those earlier described in reference to FIGS. 2, 3 and 4.

In one embodiment, the protective cover 20 includes a top sheet 22 sealed to a bottom sheet 24 by a single seal 62 so as to create a protective pouch. FIG. 5 illustrates the protective cover 20 of the present invention by itself without showing a connector therein so that the following discussion of the protective cover 20 is clearer.

In one embodiment, the top sheet 22 may be shorter in length at the proximal end than the bottom sheet 24 to provide an easily located start point for peel-away of the top sheet 22 from the bottom sheet 24. It is to be understood that in other embodiments the top sheet 22 may be longer in length at the proximal end than the bottom sheet 24, or that the top sheet 22 and bottom sheet 24 may be the same length.

Further, in one embodiment, the top sheet 22 may have a flange extension 26A, as earlier discussed in reference to FIGS. 2, 3, and 4, to assist a user in locating the proximal start point for peel-away of the protective cover 20. It is to be understood that in other embodiments the top sheet 22 may be fabricated without a flange extension 26A, and that the flange extension 26A may be differently shaped.

In one embodiment, the proximal corners 28A of the top sheet 22 may be fabricated with sharp edges. The sharp edges further facilitate separation and peel-away of the top sheet 22 from the bottom sheet 24 which, in one embodiment, may be fabricated with proximal corners 28B having rounded edges. It is to be understood that in other embodiments either or both the proximal corners 28A and the proximal corners 28B may be fabricated with rounded edges, sharp edges, or a differently patterned edge.

In one embodiment, the bottom sheet 24 may be longer in length at the proximal end 46 than the top sheet 22 to facilitate locating the start point for peel-away of the top sheet 22 from the bottom sheet 24 to expose a connector. It is to be understood that in other embodiments the bottom sheet 24 may be shorter in length than the top sheet 22, or that the bottom sheet 24 and the top sheet 22 may be the same length.

Further, in one embodiment, the bottom sheet 24 has a flange extension 26B, as earlier discussed in reference to FIGS. 2, 3, and 4, that assists a user in locating the proximal start point for peel-away of the protective cover 20. It is to be understood that in other embodiments the bottom sheet 24 may be fabricated without a flange extension 26B, and that the flange extension 26B may be differently shaped.

In one embodiment, the proximal corners 28B of the bottom sheet 24 may be fabricated with round edges. The round edges further facilitate separation and peel-away of the bottom sheet 24 from proximal corners 28A of the top sheet 22 which, in one embodiment, may be fabricated with sharp edges. It is to be understood that in other embodiments either or both the proximal corners 28B and the proximal corners 28A may be fabricated with rounded edges, sharp edges, or a differently patterned edge.

The bottom sheet 24 may be printed with markings and/or instructions for ease of use. In one embodiment, the interior face of the bottom sheet 24 may be printed with an instruction 40, such as "PEEL HERE", at the proximal end to instruct a user where to begin the proximal to distal peel-away of the top sheet 22 from the bottom sheet 24. Other printing, such as international symbols, may also be used and printed in other locations on the bottom sheet 24. The bottom sheet 24 may also be printed with positioning markings for positioning a connector within the protective cover 20. It is to be understood that in other embodiments, markings and instructions may also be printed on the exterior face of the bottom sheet 24, on either face of the top sheet 22 or may be partially or completely omitted.

In one embodiment, the top sheet 22 and bottom sheet 24 are joined by a seal 62 to form the protective cover 20. In one embodiment, the seal 62 may be a single seal that extends along both sides and across the proximal end 46 of the protective cover 20 leaving the distal end 48 of the protective cover 20 unsealed. In one example, the seal 62 may be formed using a Verton Package Sealer N#6000005. In one example, the seal 62 may be created using a high temperature set point of 220° F. (degrees Fahrenheit)±5° F., a low temperature set point of 175° F.±5° F., and a pressure of 70 PSI±5 PSI. It is to be understood that these temperature and pressure ranges may be particular to the specific sealer given above used with the particular materials described above. Other sealers may require different ranges. Other sealing methods and settings may be used, but the seals produced should be strong enough to maintain a connector in a pouched position, and yet be weak enough to allow the top sheet 22 and bottom sheet 24 to be peeled away to expose a connector for use.

In one example, after formation of the seal 62, a connector may be inserted, proximal end first, at the distal end of protective cover 20, until it stops distal to the proximal end of the seal 62. The distal end of the protective cover 20 may then be sealed to the connector where it exits distally from the protective cover 20.

Figure 6:
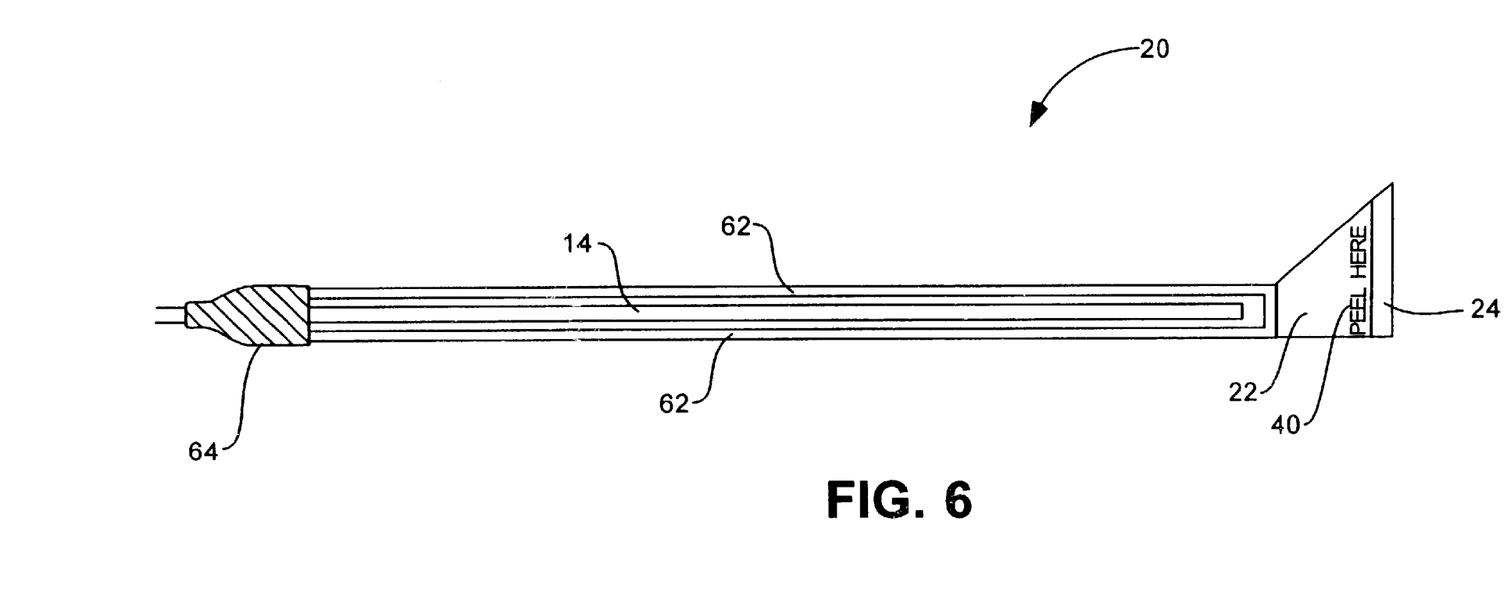
FIG. 6 illustrates a top view of a protective cover according to the embodiment of the present invention illustrated in FIG. 5 in conjunction with a connector.

FIG. 6 illustrates a top view of a protective cover according to the embodiment of the present invention illustrated in FIG. 5 in conjunction with a connector. In one example of this embodiment the connector 14 that may have a less defined connector structure, such as the termination of the catheter, i.e., an open tube structure. However, for purposes of this example, and for ease of description, the proximal end of the catheter desired to be protected from contaminants will be referred to as connector 14. It is to be understood that the connector 14 is not meant to be limiting on the present invention, but rather, merely serves as another example of a connector which may be protected from contaminants by use of the present invention.

In one example, a plurality of protective covers 20 may be fabricated in a sheet format using a standard multiple, cut and seal procedure well known by those of ordinary skill in the art in which the top sheet 22 and bottom sheet 24 are cut using a die and sealed forming multiple protective covers 20 in one sheet. The Vertron Package sealer N#6000005 may be used to form the seal 62. The individual protective covers 20 are then removed from the excess materials of the sheet and are ready to be assembled with connectors. Individual connectors 14 are then inserted, proximal end first, e.g., the end that will connect to the radiation source delivery device, into the open, distal end 48 of the protective cover 20 until the connector 14 is positioned distal to the proximal end of the seal 62.

After positioning, the open, distal end 48 of the protective cover 20 may be sealed by seal 64 to the connector 14 where it extends distal to the protective cover 20. Seal 64 may be formed using heat activated shrink-wrap so that a protective pouch is created around the connector 14 to prevent contamination of connector 14 prior to connection to a radiation source delivery device. It is to be understood that other methods of sealing the open, distal end of the protective cover 20 to the catheter may also be used. Further, it is to be understood that other embodiments of the present invention can be formed in various shapes and sizes to accommodate a variety of connectors. Additionally, other methods of assembling the protective cover 20 with the connector 14 may be used, and that the method of assembly is not meant to limit the scope of the present invention.

Figure 7:
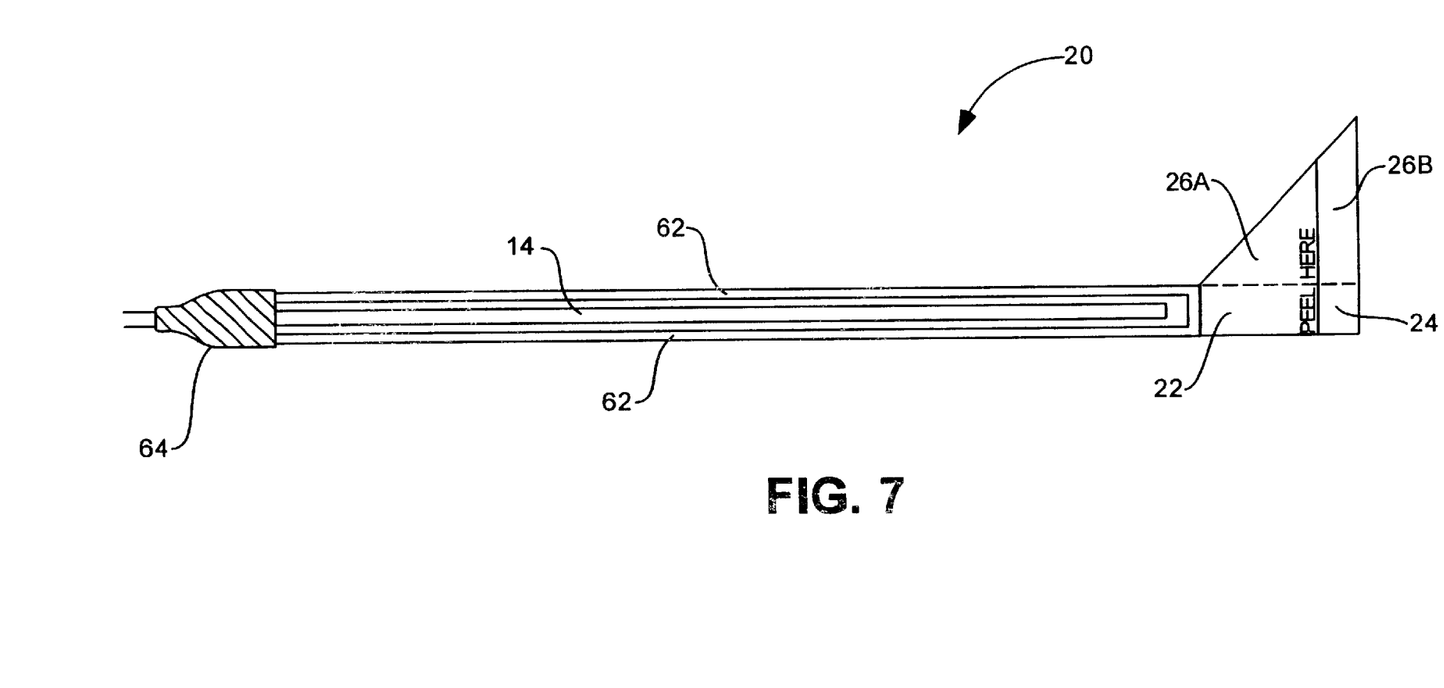
FIG. 7 illustrates a top view of a protective cover according to another embodiment of the present invention.

FIG. 7 illustrates a top view of a protective cover according to another embodiment of the present invention. The embodiment illustrated in FIG. 7 may be fabricated as earlier described with reference to FIGS. 5 and 6, however the dimensions of the flange extensions 26A and 26B are increased to facilitate the peel-away of the top sheet 22 from the bottom sheet 24.

Thus, the present invention as described herein provides several embodiments of a protective cover to help prevent contamination of a radiation source delivery device by a connector and to help prevent contamination of the connector prior to connection to the radiation source delivery device. The protective cover includes a top sheet and a bottom sheet that are sealed together to form a protective pouch around a connector. The protective cover can remain intact during the positioning of an intravascular catheter, and can then be peeled away to expose the uncontaminated connector for attachment to the radiation source delivery device. The protective cover is peeled away from the connector in a proximal to distal direction to direct contaminants away from the exposed connector.

The protective cover may be partially peeled away to provide a shielding structure to additionally help prevent contamination of the connection, or may be completely peeled away from the connector.

In the embodiments and examples presented herein, the present invention is described in relation to delivery of intravascular radiation therapy (IRT) utilizing a catheter and a radiation source delivery device. It is to be understood that the present invention may be used to protect a catheter connector from contamination prior to connection to devices other than radiation source delivery devices. Further, the present invention may also be used with intravascular procedures other than IRT where it is advantageous to prevent contamination of catheter connectors, or other connectors, used in those procedures, for example, angioplasty, atherectomy, stenting, or instrumental diagnostic procedures.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. An apparatus comprising:
   a protective cover; and
   a connector comprising a connection segment and an elongated handle,
   wherein said protective cover has dimensions selected to encompass said connection segment and a first portion of an elongated handle that is one of adapted to be coupled to and integrally configured with a catheter having dimensions suitable for placement in an intravascular vessel, wherein said connection segment has a lumen therethrough defining a first orifice and a second orifice, said first portion of said elongated handle coupled to said connection segment at said first orifice away from a device and said protective cover having a closed proximal end and an opened portion of a distal end to allow a second portion of the elongated handle of said connector to extend distally beyond the protective cover, and
   wherein said protective cover has dimensions suitable to seal said connection segment and said first portion of the elongated handle within said protective cover and at least one seal portion having a resistance force capable of maintaining said connection segment and said first portion of said elongated handle within said protective cover and to allow a user to expose said connection segment from said protective cover when said connection segment is to be coupled to said device at said second orifice.

2. The apparatus of claim 1 wherein said protective cover further includes a top sheet and a bottom sheet sealed together to form a protective pouch.

3. The apparatus of claim 2 wherein said top sheet and said bottom sheet are sealed together such that said top sheet and said bottom sheet may be separated and peeled away from said connector in a proximal to distal direction to expose said connector for attachment to said device.

4. The apparatus of claim 3 wherein said top sheet and said bottom sheet are sealed together such that said top sheet and said bottom sheet may be partially separated and partially peeled away from said connector in a proximal to distal direction to expose said connector for attachment to said device, said partially separated top and bottom sheets at least partially enveloping the connector and a mating device connector to help prevent contamination of said mating device connector when the connector is attached to the mating device connector.

5. A protective cover comprising:
a top sheet; and
a bottom sheet
wherein said top sheet and said bottom sheet are coupled along at least one seal portion forming a protective pouch having dimensions selected to encompass a connector comprising a connection segment and a first portion of an elongated handle that is one of adapted to be coupled to and integrally configured with a catheter having dimensions suitable for placement in an intravascular vessel,
wherein said connection segment has a lumen therethrough defining a first orifice and a second orifice, and said first portion of said elongated handle is coupled to said connection segment at said first orifice,
wherein said protective pouch is formed when said connection segment is positioned between said top sheet and said bottom sheet to seal said connection segment and said first portion of said elongated handle away from a device, said top sheet and said bottom sheet each has a proximal end and a distal end in which a portion of said distal ends define an opening to allow a second portion of the elongated handle to extend beyond the protective cover, and
wherein said at least one seal portion couples said top sheet and said bottom sheet with a resistance force capable of maintaining said connection segment and said first portion of said elongated handle within said protective pouch and such that said top sheet and said bottom sheet may be separated and peeled away from said connection segment by a user in a proximal to distal direction to expose said connection segment to couple said connection segment to said device at said second orifice.

6. The protective cover of claim 5 further comprising intermediate stops so that said top sheet may be partially peeled away from said bottom sheet in a proximal to distal direction.

7. The protective cover of claim 5 wherein said top sheet is transparent and said bottom sheet is opaque.

8. The protective cover of claim 5 wherein said top sheet is waterproof and said bottom sheet is water-resistant.

9. A protective cover comprising:
a top sheet, said top sheet having a proximal end and a distal end; and
a bottom sheet, said bottom sheet having a proximal end and a distal end,
wherein said top sheet and said bottom sheet are coupled along at least one seal portion to form a protective pouch having dimensions selected to encompass a connector comprising a connection segment and a first portion of an elongated handle that is one of adapted to be coupled to and integrally configured with a catheter having dimensions suitable for placement in an intravascular vessel,
wherein said connection segment has a lumen therethrough defining a first orifice and a second orifice, said first portion of said elongated handle coupled to said connection segment at said first orifice device, said protective pouch formed when said connection segment is positioned between said top sheet and said bottom sheet to seal said connection segment and said first portion of said elongated handle away from a device,
wherein said at least one seal portion couples said top sheet and said bottom sheet such that the protective pouch comprises a closed proximal end formed by the proximal ends of the said top sheet and said bottom sheet and such that a portion of said distal ends of said top sheet and said bottom sheet define an opening to allow a second portion of the elongated handle to extend beyond the protective pouch, and
wherein said at least one seal portion has a resistance force capable of maintaining the connection segment and said first portion of said elongated handle within said protective cover and to allow a user to expose in a proximal to distal direction said connection segment from said protective pouch to allow a user to couple said connection segment to said device at said second orifice.

10. The protective cover of claim 9 wherein said proximal end of said top sheet is shorter than said proximal end of said bottom sheet.

11. The protective cover of claim 9 wherein said top sheet and said bottom sheet have flange extensions at said proximal ends.

12. The protective cover of claim 11 wherein said proximal end of said top sheet has sharp edges and said proximal end of said bottom sheet has rounded edges.

13. The protective cover of claim 9 wherein said top sheet further comprises an exterior face and an interior face, wherein said interior face provides a friction surface to allow easy gripping of said top sheet.

14. The protective cover of claim 9 wherein said bottom sheet further comprises an exterior face and an interior face, wherein said interior face has printed positioning markers.

15. The protective cover of claim 9 wherein said top sheet is transparent and said bottom sheet is opaque.

16. The protective cover of claim 9 wherein said top sheet is waterproof and said bottom sheet is water-resistant.

17. The protective cover of claim 15 wherein said top sheet is fabricated from 2-ply 200 low density polyethylene and 48 gauge polyethylene terephthalate.

18. The protective cover of claim 15 wherein said bottom sheet is fabricated from an opaque, flexible, water resistant material having the ability to allow gas to permeate through its surface, said material having a CR-27 coating.

19. The protective cover of claim 15 wherein said bottom sheet is fabricated from an opaque, flexible, water resistant material having the ability to allow gas to permeate through its surface, said material having an ITP150 coating.

20. An apparatus comprising:
a connector comprising a connection segment having a lumen therethrough defining a first orifice and a second orifice, said connection segment coupled to a first portion of an elongated handle at said first orifice, said elongated handle that is one of adapted to be coupled to and integrally configured with a catheter having dimension suitable for placement in an intravascular vessel; and
a protective cover having dimensions selected to encompass said connection segment and a first portion of said elongated handle away from a device, said protective cover having a proximal end and a distal end in which a portion of said distal end defines an opening to allow a second portion of the elongated handle to extend beyond the protective cover, said protective cover comprising a seal portion having a resistance force capable of maintaining said connection segment and said first portion of said elongated handle within said protective cover and to allow a user to expose said connection segment from said protective cover when said connection segment is to be coupled to said device at said second orifice.

21. The apparatus of claim 20 wherein said protective cover further comprises a top sheet and a bottom sheet sealed together to form a protective pouch around said connector.

22. The apparatus of claim 21 wherein said top sheet and said bottom sheet are sealed together such that said top sheet and said bottom sheet may be separated and peeled away from said connector in a proximal to distal direction to expose said connector for attachment to said device.

23. The apparatus of claim 22 further comprising intermediate stops to allow said top sheet to be partially peeled apart from said bottom sheet in a proximal to distal direction to expose said connector, said connector to couple to a mating connector of said device, said partially peeled apart top and bottom sheets at least partially enveloping the connector and the mating connector to help prevent contamination of said connector and mating connector when coupled.

24. The apparatus of claim 21 wherein said top sheet is transparent and said bottom sheet is opaque.

25. The apparatus of claim 24 wherein said top sheet is fabricated from 2-ply 200 LDPE and 48 gauge PET.

26. The apparatus of claim 24 wherein said bottom sheet is fabricated from an opaque, flexible, water resistant material having the ability to allow gas to permeate through its surface, said material having a CR-27 coating.

27. The apparatus of claim 24 wherein said bottom sheet is fabricated from an opaque, flexible, water resistant material having the ability to allow gas to permeate through its surface, said material having an ITP150 coating.

* * * * *